United States Patent [19]
Barrett

[11] Patent Number: 5,141,505
[45] Date of Patent: Aug. 25, 1992

[54] GARMENT ASSEMBLY WITH ATTACHED BAG FOR ENCLOSING THE GARMENT WHEN SOILED

[76] Inventor: Peter Barrett, 203 Pidgeon Hill Rd., Huntington Station, N.Y. 11746

[21] Appl. No.: 735,944

[22] Filed: Jul. 25, 1991

[51] Int. Cl.⁵ .................... A61F 13/15; A61F 13/20
[52] U.S. Cl. .................... 604/385.1; 604/396
[58] Field of Search .......... 604/385.1, 385.2, 386, 604/387, 389, 396

[56] References Cited

U.S. PATENT DOCUMENTS

| | | | |
|---|---|---|---|
| 3,230,956 | 1/1966 | Kargul | 604/385.1 |
| 3,274,999 | 9/1966 | Robinson | 604/385.1 X |
| 3,369,545 | 2/1968 | Wanberg | 604/385.1 |
| 3,604,423 | 9/1971 | Fraser | 604/385.1 |
| 3,731,689 | 5/1973 | Schaar | 604/385.1 |
| 3,865,110 | 2/1975 | Traverse | 604/385.1 X |
| 3,877,432 | 4/1975 | Gellert | 604/385.1 |
| 3,920,019 | 11/1975 | Schaar | 604/385.1 |
| 4,085,753 | 4/1978 | Gellert | 604/385.1 X |
| 4,182,336 | 1/1980 | Black | 604/385.1 |
| 4,430,087 | 2/1984 | Azpiri | 604/385.1 |
| 4,493,713 | 1/1985 | Izzo | 604/385.1 |
| 4,605,403 | 8/1986 | Tucker | 604/385.1 |
| 4,674,135 | 6/1987 | Greene | 604/385.1 X |
| 4,692,162 | 9/1987 | Binker et al. | 604/385.1 |
| 4,743,240 | 5/1988 | Powell | 604/385.1 |
| 4,753,647 | 6/1988 | Curtis | 604/385.1 |
| 4,790,839 | 12/1988 | Ahr | 604/385.1 X |
| 4,790,840 | 12/1988 | Cortina | 604/385.1 |
| 4,808,175 | 2/1989 | Hansen | 604/385.1 |
| 4,857,066 | 8/1989 | Allison | 604/385.1 |
| 4,923,455 | 5/1990 | Dean et al. | 604/385.1 |
| 4,931,052 | 6/1990 | Feldman | 604/385.1 |
| 4,964,859 | 10/1990 | Feldman | 604/385.1 |
| 4,968,311 | 11/1990 | Chickening et al. | 604/385.1 |
| 4,968,312 | 11/1990 | Khan | 604/385.1 |

*Primary Examiner*—David J. Isabella
*Assistant Examiner*—Elizabeth M. Burke
*Attorney, Agent, or Firm*—Edward H. Loveman

[57] ABSTRACT

A garment assembly which includes a garment such as a diaper or underpants subject to be soiled by the user. Attached to the back of the garment is the closed end of a nonporous bag. The remainder of the bag in flat, rolled or unrolled position is temporarily attached to the garment. After the garment becomes soiled and is removed from the wearer, it can be folded into a generally rectangular form. The bag can be extended and turned inside out to enclose the soiled garment. The free end of the bag can be sealed closed to form a compact, flat, leakproof, odor-free, safe, sanitary, package. This package can be safely transported and can be disposed at a later time in an ecologically approved manner.

6 Claims, 3 Drawing Sheets

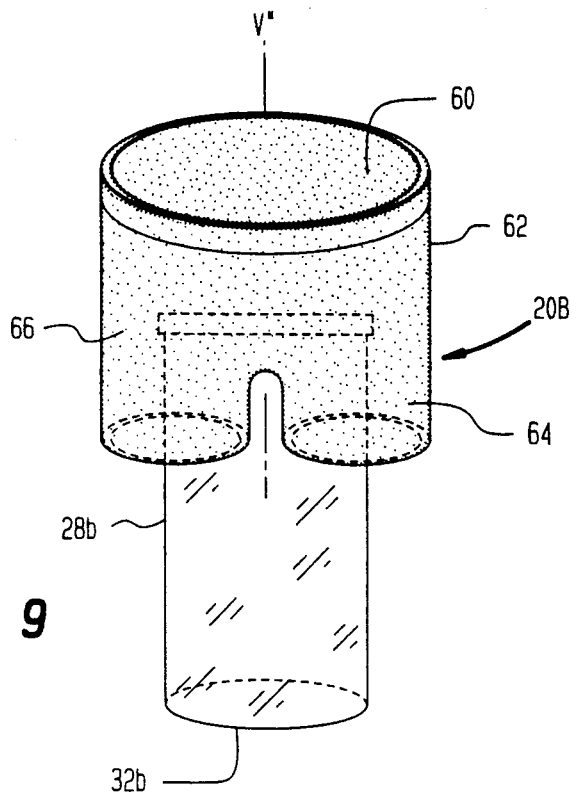
FIG. 9
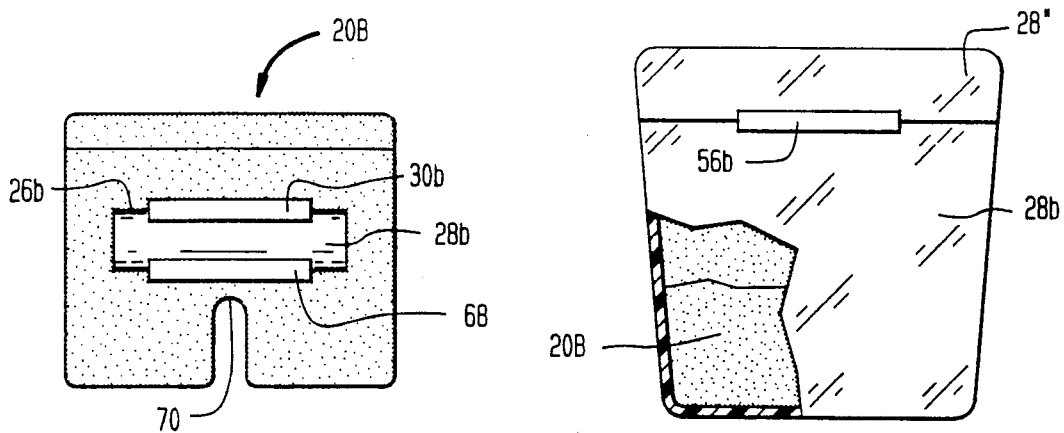
FIG. 10
FIG. 12

5,141,505

GARMENT ASSEMBLY WITH ATTACHED BAG FOR ENCLOSING THE GARMENT WHEN SOILED

BACKGROUND OF THE INVENTION

1. Field of the Invention

This invention relates to garments subject to becoming soiled in use, especially diapers and underclothing and more particularly concerns a garment assembly consisting of a garment and an attached nonporous bag on the back of the garment, and more specifically concerns a garment assembly of a garment and attached nonporous bag large enough to be reversed ie turned inside out to close the garment after it becomes soiled and is removed from the wearer.

When parents are travelling with infants, considerable difficulty is experienced in disposing of soiled diapers in a safe, sanitary, leakproof, odor-free manner. The same difficulty is encountered in maternity wards of hospitals where large numbers of diapers are soiled daily and must be disposed of in the most sanitary way possible. Similar difficulties are experienced in hospitals where there are patients wearing undergarments who suffer from HIV, incontinence of urine, fecal matter, and body discharges such as blood, pus, mucous, etc. Generally the soiled diapers and undergarments are thrown haphazardly into hampers in a very disorderly fashion where they can fall out, and are free to emit odors, leak toxic fluids, etc.

SUMMARY OF THE INVENTION

According to the invention there is provided a garment assembly, comprising a garment such as a diaper or underpants having a nonporous outer side. On the back of the garment is permanently secured the closed end of a nonporous bag. The bag can be attached in a flat, rolled or unrolled position, and held in place by temporary attachment means. When the garment becomes soiled, the bag can be extended and turned inside out to enclose the garment. The garment can be folded to flat, rectangular configuration before being inserted into the reversed bag. This will form a compact, flat package which can be carried about, or stored in a safe, sanitary, odor-free manner until the package can be disposed of in an ecologically approved manner by incineration, recycling, etc.

These and other objects and many of the attendant advantages of this invention will be readily appreciated as the same becomes better understood by reference to the following detailed description when considered in connection with the accompanying drawings in which:

BRIEF DESCRIPTION OF THE DRAWINGS

FIG. 10 is a rear elevational view of an undergarment, namely underpants, on the back of which is mounted a disposable bag according to the invention;

FIG. 11 is a perspective view of the underpants of FIG. 10, with bag in extended position; and FIG. 12 is a front elevational view of the disposable bag of FIGS. 10 and 11 shown enclosing the soiled underpants.

DESCRIPTION OF THE PREFERRED EMBODIMENTS

Figure 1:
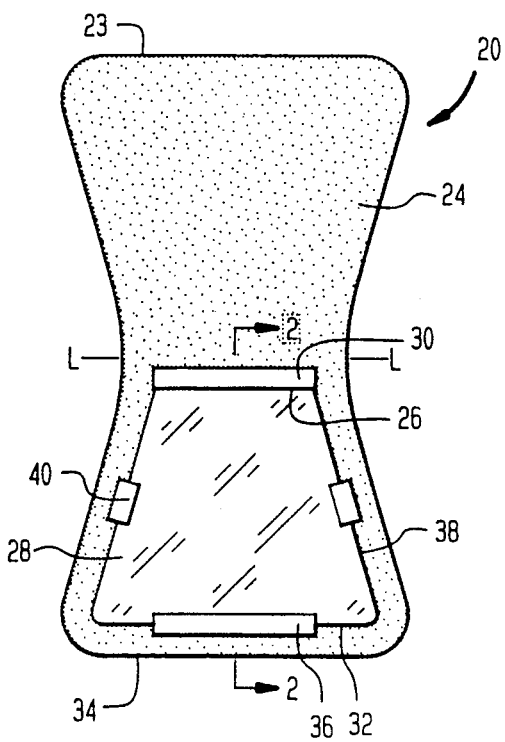
FIG. 1 is a rear elevational view of a diaper with an attached disposal bag in accordance with the invention.
Figure 2:
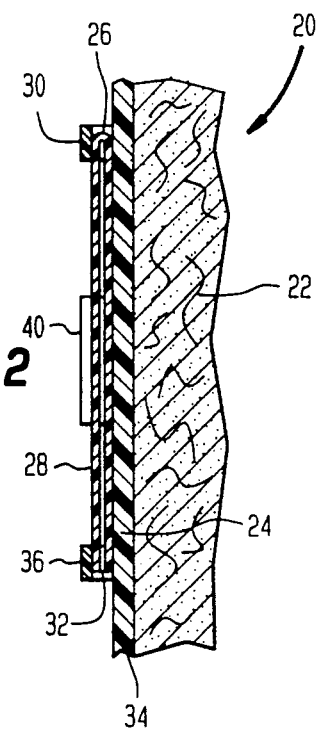
FIG. 2 is an enlarged fragmentary sectional view taken along line 2—2 of FIG. 1.

Referring now to the drawings wherein like reference characters designate like or corresponding parts throughout, there is illustrated in FIGS. 1 and 2, a conventional type of diaper 20 such as generally used for an infant. The diaper has a fibrous front panel 22 which is moisture absorbent and during use is placed against the body of the infant. Secured to the front panel 22 is a nonporous liner or backing panel 24. Near a transverse center line L—L of the back panel 24 is secured a narrow end 26 of a flat disposable bag 28. The narrow end 26 is closed and is secured permanently by an adhesive tape 30 near or along the line L—L. Instead of adhesive tape the closed end of the bag 28 can be secured to the back panel 24 by heat sealing, electronic sewing, stitching or a strong adhesive without the tape 30.

Disposable bag 28 may be generally trapezoidal in configuration with a wider end open end 32 secured temporarily to the panel 24 near the edge by a removable adhesive tape 36. The open end 32 is straight and parallel to the narrow closed end 26. The bag 28 has slanted, closed side edges 38 which flare outwardly and extend from the opposite ends of the closed end or edge 26 to terminate at opposite ends of the longer open end 32. Adhesive strips or tabs 40 can be used for temporarily attaching the edges 38 to the back of the panel 24.

Figure 3:
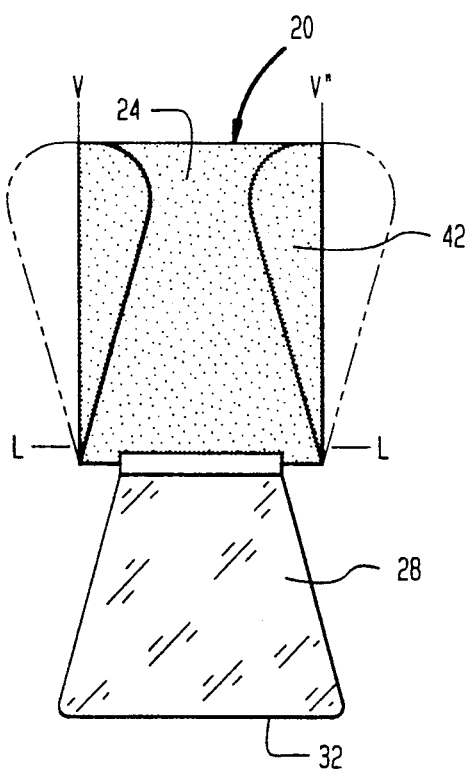
FIG. 3 is a front elevational view of the diaper of FIG. 1 in soiled condition, and folded position of insertion into the extended disposable bag.
Figure 4:
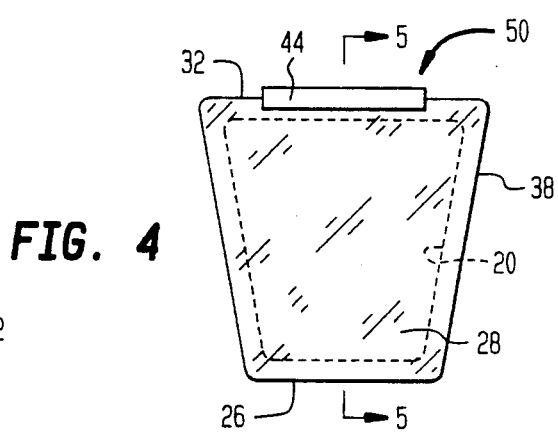
FIG. 4 is a elevational view of the disposable bag containing the soiled diaper of FIGS. 1-3.
Figure 5:
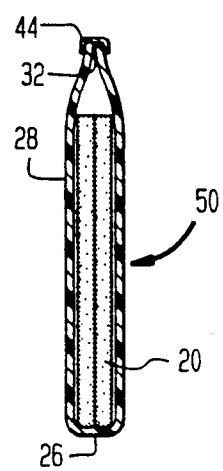
FIG. 5 is an enlarged central sectional view taken along line 5—5 of FIG. 4.

In FIG. 3 the diaper 20 is shown folded in half on the line L—L for use in conventional manner. After it is soiled and removed from the infant, lateral flaps 42 of the diaper 20 can be folded inwardly on lines V, V' so the diaper 20 has a flat, generally rectangular configuration. The adhesive strips 36 and 40 are removed so that the disposable bag 28 extends away from the diaper 2. In this position, the bag 28 can be turned inside out and the entire folded diaper 20 can be inserted into the reversed bag 28 as shown in FIGS. 4 and 5. An adhesive strip 44 can be applied to the open top of the bag 28 to close the bag 28 and make a compact package 50. The bag 28 encloses the folded soiled diaper neatly and compactly.

Although not shown, if desired, the disposable bag 28 may have the closed end 26 secured near a top edge 23 of the diaper 20 with the open end secured thereto at the line L—L with the tape 36 and side edges secured to the diaper 20 by the tape 40. After the diaper is soiled and removed from the infant, tapes 36 and 40 are removed and the bag 28 extended above the top edge 23. The bag 28 may then be turned inside out and the entire diaper 20 inserted into the reversed bag. As before, an adhesive strip 44 may be applied to the open top of the bag 28 to close the bag 28 and make a compact package 50.

The package 50 can be placed in a hamper or other container. A plurality of closed, sealed, packaged diapers can be stored in a hamper in a neat, compact, safe way until all are ready to be disposed of in a proper, ecologically approved manner, such as by incineration, recycling, etc.

Figure 6:
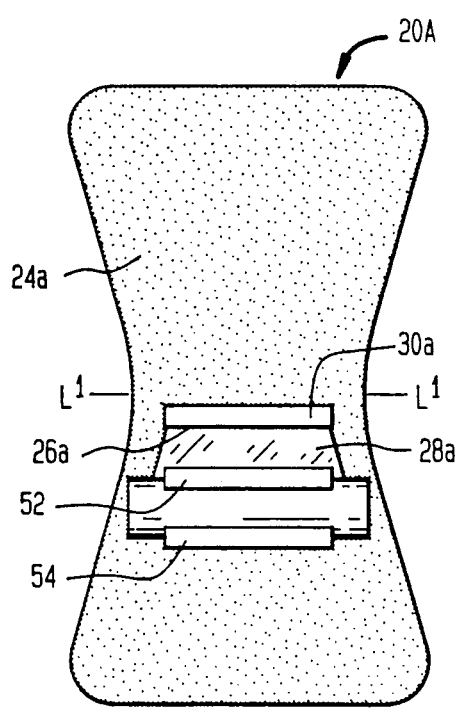
FIG. 6 is a rear elevational view of another diaper with another attached disposable bag according to the invention.
Figure 7:
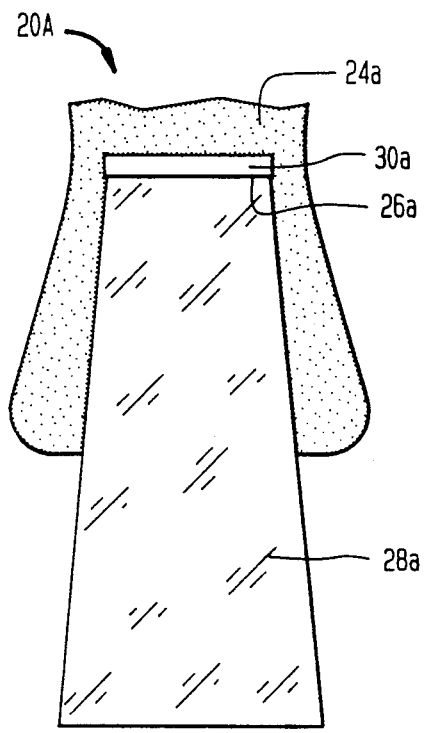
FIG. 7 is a rear elevational view similar to a portion of FIG. 6, with disposable bag shown in extended position.
Figure 8:
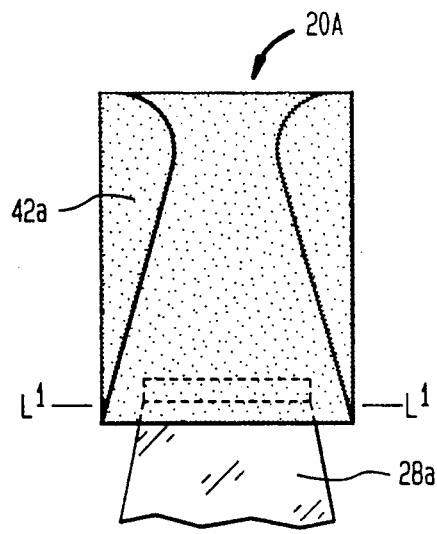
FIG. 8 is a front elevational view of a soiled, folded diaper ready for enclosure in an extended disposable bag turned inside out.
Figure 9:
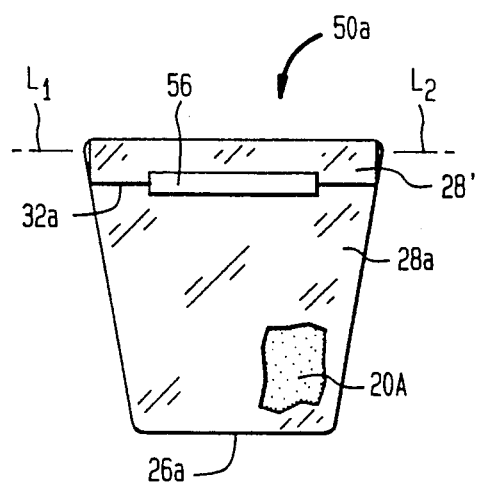
FIG. 9 is a front elevational view of the closed bag of FIGS. 6-8 containing the soiled diaper.

In FIG. 6 is shown another diaper 20A which is larger than the diaper 20 generally employed for infants. Diaper 20A is intended for a larger child. A closed end 26a of a disposable bag 28a is secured ny an adhesive tape 30a permanently to a back 24a of the diaper 20A. The bag 28a can be rolled up or folded neatly and held be a temporary adhesive strips 52 and 54. FIG. 7 shows the bag 28a in fully extended position with the strips 52 and 54 removed. The overall length of the bag 28a is approximately equal to the unfolded length of the diaper 20A. The bag 28a is at least twice the length of the bag 28 employed with the diaper 20. In FIG. 8 the diaper 20A is shown in folded position after being used and soiled. The diaper 20A is folded along a central transverse line L1, L2 and lateral flaps 42a are turned inwardly so that the diaper has a generally rectangular configuration. The bag 28a extended as shown FIGS. 7 and 8 can be turned inside out to enclosed the diaper 20A in a closed, compact package 50a. An excess length 28' of bag 28a folded down an transverse line L1-L2 over open end 32a to form a flap which can be held in place by an adhesive tape 56.

In FIGS. 10, 11 and 12 are shown a very useful application of the invention. Here there is shown a pair of underpants 20B such as used by a patient who suffers from HIV incontinence of urine, fecal matter, and other body discharges such as blood, pus, mucous. The underpants 20B has a highly porous inner lining 60 covering a cylindrical body 62 and a pair of legs 64. The outer layer 66 of the underpants 20B is nonporous. Attached to the back of the underpants 20B is a rolled up disposable bag 28b as shown in FIG. 10. The bag 28b is held by permanent adhesive tape 30b secured to the closed end 26b of the bag 28b which is shown fully rolled up so that it can be held by a temporary tape 68 just above a crotch 70 of the underpants 20B. In FIG. 11 the bag 28b is shown fully extended with an open end 32b free at the bottom. When the underpants 20B becomes soiled it is removed from the patient. The bag 28b is extended as shown in FIG. 11 and then is turned inside out to enclose the underpants 20B. The underpants 20B can be folded on a vertical line V'' to compact form. FIG. 12 shows the bag 28b wholly enclosing the soiled underpants 20B. An excess flap 28'' can be folded down and secured by adhesive tape 56b.

All the forms of the invention described enable the soiled garment to be folded neatly and then inserted into the reversed disposal bag to form a flat, compact unit. A plurality of soiled garments can be stored in a hamper in neat, orderly fashion. This contrasts with the prior condition where soiled unwrapped garments are tossed haphazardly into a hamper. This unsafe practice exposes the soiled garments to the air and to each other and can result in spread of disease germs. The present invention neatly packages each soiled garment until it can be safely disposed in a approved manner.

The present invention adds nothing to the cost of the garment except for the inexpensive attached nonporous disposable bag The disposable bag in folded. flat or rolled position, does not interfere with the normal use of the garment. But when the garment is soiled, the disposable bag is instantly releasable and available to enclose the soiled garment.

It should be understood that the foregoing relates to only a limited number of preferred embodiments of the invention which have been shown by way of example only and that it is intended to cover all changes and modifications of the examples of the invention herein chosen for the purpose of the disclosure, which do not constitute departures from the spirit and scope of the invention.

I claim:

1. A garment assembly configured for deposition in a safe sanitary, odor-free manner after becoming soiled, comprising:

a garment having a front panel, a back panel having inner and outer surfaces, and a crotch portion said garment mountable on a lower portion of a body of a wearer with said front panel adjacent said body;

a disposable bag having a closed end, an opposite, unsecured open end and opposite, unsecured closed sides, said closed end being laterally permanently secured across the outer surface of said back panel of said garment near said crotch portion,;

temporary attachment means holding said unsecured open end and said unsecured closed sides of said bag in flat deposition against said back panel of said garment so that said garment can be used in a normal manner, and whereby said temporary attachment means are removed so that said bag can be extended when said garment is soiled and said bag can be turned inside out to enclose said soiled garment completely in a sanitary, odor-free way for deposition in an ecologically approved manner.

2. A garment assembly as claimed in claim 1, wherein said garment is a diaper having a length and wherein said bag has a length one half the length of said diaper, so that said bag is attached to said diaper in flat unfolded position until it is required to be reversed inside out to enclose said diaper when soiled.

3. A garment assembly as claimed in claim 1, wherein said garment is a diaper having a length and wherein said bag has a length equal to the length of said diaper, so that said bag is attached to said diaper in a flat rolled position until it is required to be extended and reversed inside out to enclose said diaper when said diaper is soiled.

4. A garment assembly as claimed in claim 1, wherein said garment is underpants having a cylindrical body with attached short legs, said garment having a porous inner liner and a non-porous outer liner, said bag having a length greater than that of said underpants, so that said underpants can be folded flat after becoming soiled, and so that said bag can be extended and reversed inside out to enclose the folded, soiled underpants.

5. A garment assembly as claimed in claim 1 wherein said bag is made of a thin light nonporous material to prevent leakage and escape of odors and toxic material from said soiled garment in said bag.

6. A garment assembly as claimed in claim 1, wherein said bag is trapezoidal in configuration with a narrow closed end secured permanently to said garment and unsecured, closed flaring edges and a free wider open end to facilitate turning said bag inside out and enclosing said soiled garment therein.

* * * * *